(12) United States Patent
Von Malmborg

(10) Patent No.: US 9,566,418 B2
(45) Date of Patent: Feb. 14, 2017

(54) SENSOR GUIDE WIRE WITH MICRO-CABLE WINDING

(75) Inventor: Pär Von Malmborg, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 292 days.

(21) Appl. No.: 12/739,290

(22) PCT Filed: Oct. 24, 2008

(86) PCT No.: PCT/SE2008/051210
§ 371 (c)(1),
(2), (4) Date: Apr. 22, 2010

(87) PCT Pub. No.: WO2009/054802
PCT Pub. Date: Apr. 30, 2009

(65) Prior Publication Data
US 2010/0228112 A1    Sep. 9, 2010

Related U.S. Application Data

(60) Provisional application No. 60/996,065, filed on Oct. 26, 2007.

(51) Int. Cl.
*A61B 5/04*        (2006.01)
*A61M 25/09*    (2006.01)
*A61B 5/0215*  (2006.01)
*A61B 5/00*      (2006.01)
*A61B 17/22*    (2006.01)

(52) U.S. Cl.
CPC ............ *A61M 25/09* (2013.01); *A61B 5/0215* (2013.01); *A61B 5/6851* (2013.01); *A61B 2017/22038* (2013.01); *A61B 2562/028* (2013.01); *A61M 2025/09133* (2013.01); *A61M 2025/09183* (2013.01)

(58) Field of Classification Search
CPC ..... A61M 25/09; A61B 5/0215; A61B 5/6851
USPC ....... 600/373, 357, 486, 500, 504–507, 301, 600/465, 466, 467, 480, 481, 485, 488
See application file for complete search history.

(56) References Cited

U.S. PATENT DOCUMENTS 4,286,217 A * 8/1981 Planche et al. ............... 324/347
4,481,953 A * 11/1984 Gold ...................... A61N 1/056
600/374

(Continued)

FOREIGN PATENT DOCUMENTS

EP    0 652 026 A1    5/1995
EP    0 806 219 B1    11/1997

(Continued)

*Primary Examiner* — Jacqueline Cheng
*Assistant Examiner* — Puya Agahi
(74) *Attorney, Agent, or Firm* — Foley & Lardner LLP

(57) ABSTRACT

A sensor guide wire for an intravascular measurement of a physiological variable in a living body includes a sensor region in a distal part of the sensor guide wire, a sensor element arranged in the sensor region, a male connector at a proximal part of the sensor guide wire, a least one electrical micro-cable connecting the male connector to the sensor element, and an elongated guide wire body arranged between the sensor region and the male connector. The at least one electrical micro-cable extends essentially helically around the guide wire body along the length of at least a part of the guide wire.

34 Claims, 5 Drawing Sheets

(56) References Cited

U.S. PATENT DOCUMENTS

| | | | |
|---|---|---|---|
| 4,771,782 A * | 9/1988 | Millar | 600/486 |
| 4,941,473 A * | 7/1990 | Tenerz et al. | 600/486 |
| 4,967,753 A | 11/1990 | Haase et al. | |
| 5,105,818 A * | 4/1992 | Christian et al. | 600/463 |
| 5,226,423 A * | 7/1993 | Tenerz et al. | 600/486 |
| 5,330,518 A * | 7/1994 | Neilson et al. | 607/101 |
| 5,797,856 A * | 8/1998 | Frisbie | A61M 25/09 600/585 |
| 5,938,624 A * | 8/1999 | Akerfeldt et al. | 600/585 |
| 6,142,958 A * | 11/2000 | Hammarstrom et al. | 600/585 |
| 6,167,763 B1 | 1/2001 | Tenerz et al. | |
| 6,210,339 B1 * | 4/2001 | Kiepen et al. | 600/486 |
| 6,336,906 B1 * | 1/2002 | Hammarstrom et al. | 600/585 |
| 6,549,812 B1 * | 4/2003 | Smits | 607/122 |
| 7,676,910 B2 * | 3/2010 | Kiepen et al. | 29/825 |
| 2002/0177783 A1 * | 11/2002 | Khalil | 600/505 |
| 2003/0088193 A1 * | 5/2003 | Malmborg et al. | 600/585 |
| 2004/0116816 A1 * | 6/2004 | Tenerz et al. | 600/486 |
| 2004/0180581 A1 * | 9/2004 | von Malmborg et al. | 439/669 |
| 2005/0096665 A1 | 5/2005 | Reynolds et al. | |
| 2005/0186848 A1 * | 8/2005 | von Malmborg et al. | 439/610 |
| 2006/0074318 A1 * | 4/2006 | Ahmed et al. | 600/585 |
| 2006/0074471 A1 * | 4/2006 | Palm | 607/122 |
| 2006/0122682 A1 * | 6/2006 | Sommer et al. | 607/127 |
| 2006/0189896 A1 | 8/2006 | Davis et al. | |
| 2006/0200216 A1 * | 9/2006 | Calzada et al. | 607/116 |
| 2007/0106142 A1 * | 5/2007 | Von Malmborg et al. | 600/373 |
| 2007/0135718 A1 * | 6/2007 | Corl et al. | 600/486 |
| 2007/0255144 A1 * | 11/2007 | Tulkki et al. | 600/481 |
| 2007/0255145 A1 * | 11/2007 | Smith et al. | 600/485 |
| 2008/0008688 A1 * | 1/2008 | Stokes et al. | 424/93.21 |
| 2008/0077050 A1 * | 3/2008 | Von Malmborg et al. | 600/585 |
| 2008/0119758 A1 * | 5/2008 | Samuelsson et al. | 600/561 |

FOREIGN PATENT DOCUMENTS

| | | |
|---|---|---|
| EP | 1 475 036 B1 | 11/2004 |
| WO | WO 00/57944 A1 | 10/2000 |

* cited by examiner

SECTION A-A

SECTION B-B

SECTION A-A

SECTION A-A

SECTION B-B

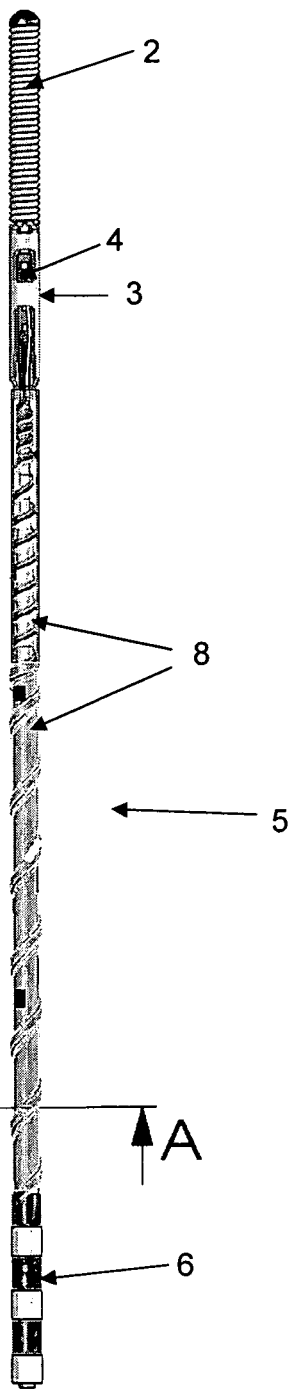
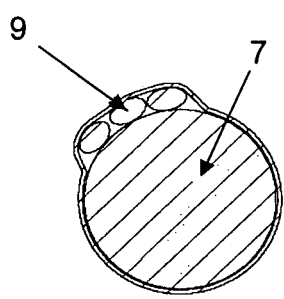
SECTION A-A FIG. 10
FIG. 11

SENSOR GUIDE WIRE WITH MICRO-CABLE WINDING

FIELD OF THE INVENTION

The present invention relates to a sensor guide wire for intravascular measurements of a physiological variable in a living body.

BACKGROUND OF THE INVENTION

In many medical procedures, various physiological conditions present within a body cavity need to be monitored. These physiological conditions are typically physical in nature—such as pressure, temperature, rate-of-fluid flow, and provide the physician or medical technician with critical information as to the status of a patient's condition.

One device that is widely used to monitor conditions is the blood pressure sensor. The sensor is typically included in a guide wire for intravascular measurements. A blood pressure sensor senses the magnitude of a patient's blood pressure, and converts it into a representative electrical signal that is transmitted to the exterior of the patient. For most applications it is also required that the sensor is electrically energized.

Some means of signal and energy transmission is thus required, and most commonly extremely thin electrical cables are provided inside the guide wire, which itself is provided in the form of a tube (in the order of 0.35 mm in outer diameter), oftentimes made of stainless steel. In order to increase the bending strength of the tubular guide wire, a core wire is positioned inside the tube. The mentioned electrical cables are positioned in the space between the inner lumen wall and the core wire.

A large flexibility of the sensor guide is advantageous in that it allows the sensor guide to be introduced into small and tortuous vessels. It should, however, also be recognized that if the core wire is too flexible, it would be difficult to push the sensor guide forward into the vessels, i.e. the sensor guide must possess a certain "pushability". Furthermore, the sensor guide must be able to withstand the mechanical stress exerted on the core wire especially in sharp vessel bends.

EP patent 1 475 036, assigned to the same assignee as in the present application, shows a sensor wire assembly, where electrical micro-cables extend along a core wire and along the length of a guide wire. One drawback with this design is that the guide wire when rotated has a tendency to store the elastic energy or the built up torque and release it, resulting in a rotational whipping.

The object of the present invention is to achieve an improved sensor guide wire that has a more predictable movement pattern compared to prior art sensor guide wires.

SUMMARY OF THE INVENTION

The above-mentioned object is achieved by a sensor guide wire for intravascular measurements of a physiological variable in a living body, comprising a sensor region in a distal part of the sensor guide wire, a sensor element arranged in said sensor region, a male connector at a proximal part of the sensor guide wire, a least one electrical micro-cable connecting the male connector to the sensor element, and an elongated guide wire body arranged between the sensor region and the male connector, wherein the at least one electrical micro-cable extends essentially helically around the guide wire body along the length of at least a part of the guide wire.

The inventor has realized that the stored energy or the build up torque that when released may result in a whipping, depends inter alia of non-symmetric geometry of the sensor guide wire and that the core wire is relatively thin in relation to the sensor guide wire. A solution to this problem according to the present invention is to make the sensor guide wire rotationally symmetric, or at least construct the sensor guide wire such that the sensor guide wire behaves as it was rotationally symmetric when guided in bent vessel geometry vessels, by winding the micro-cable around the guide wire body. This arrangement gives the guide wire a quasi-rotational symmetry and prevents the tendency to build up torque. This also makes it possible to make the core wire thicker in some embodiments. The steerability of the guide wire is thus also improved.

When the expression "electrical micro-cable" is used, it means a very thin electrical cable.

SHORT DESCRIPTION OF THE APPENDED DRAWINGS

FIG. 10 shows a fourth embodiment of the present invention.

FIG. 11 shows a transverse cross-section of the sensor and guide wire assembly taken along A-A in FIG. 10.

Throughout the figures the same reference sign designates the same, or essentially the same, feature.

DETAILED DESCRIPTION OF PREFERRED EMBODIMENTS OF THE INVENTION

Figure 1:
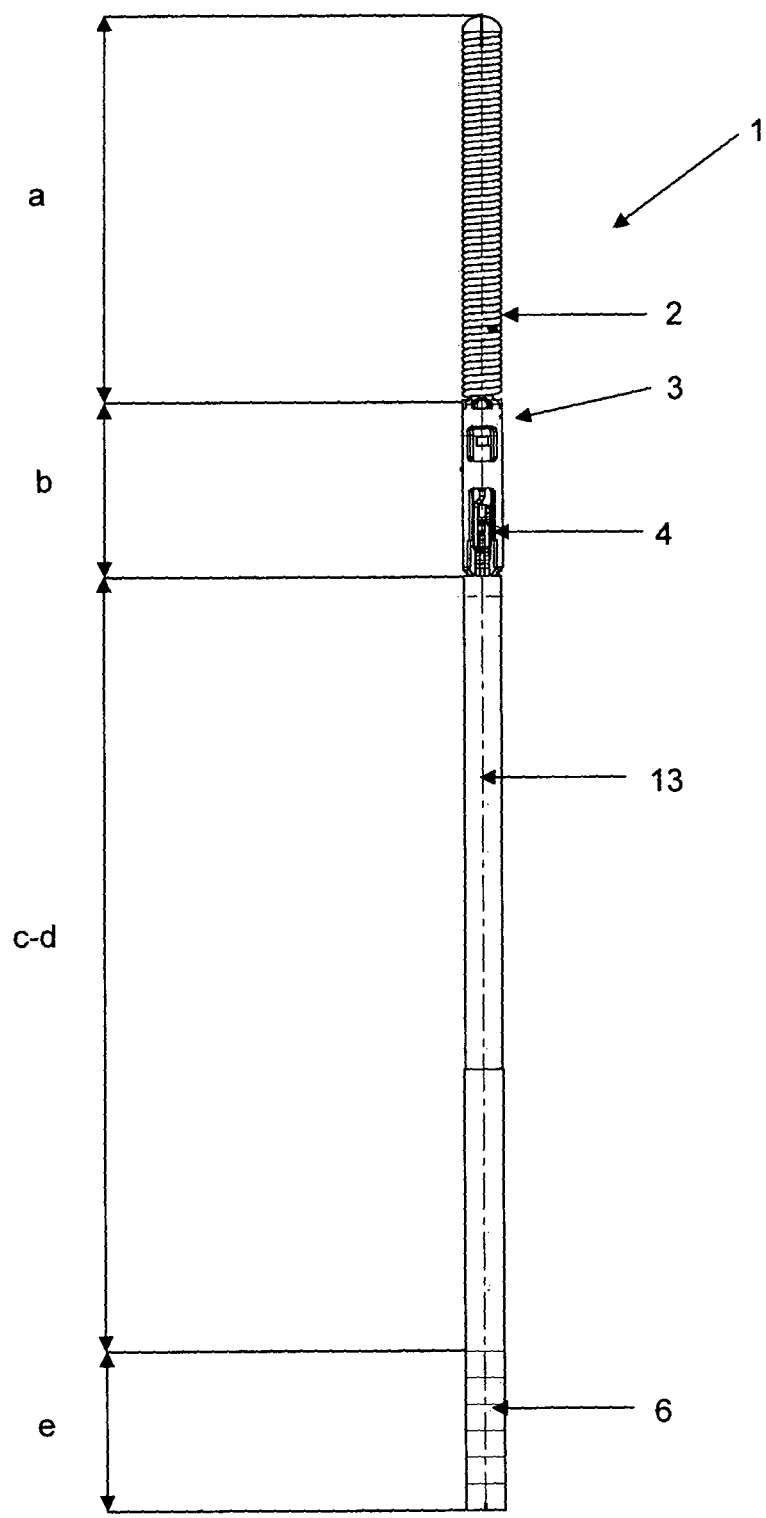
FIG. 1 shows a sensor and guide wire 1 assembly divided in different regions.

With reference to FIG. 1, a sensor guide wire 1 e.g. as exemplified by the above-mentioned EP-1 475 036 is shown. The guide wire 1 has been divided in different regions, a-e, where region a is the most distal region and e is the most proximal region. The different regions are: a) Tip region, b) Sensor region, c) Flexible region, d) Shaft region, and e) Male connector region. In an exemplary embodiment, region a) is about 10-50 mm, region b) is about 1-5 mm, region c) is about 150-400 mm, region d) is about 1000-2000 mm and region e) is about 10-100 mm. The diameter of the sensor guide wire 1 preferably varies between 0.25-2.5 mm; for use in coronary arteries, the diameter is normally 0.35 mm.

The tip region includes a radioopaque tip 2, in this embodiment in the shape of a coil. The tip region bridges to the sensor region, which includes a sensor element 4 accommodated in a jacket 3. In order to power the sensor element 4 and to communicate signals representing the measured physiological variable, one or many micro-cables or leads 9 (not shown in FIG. 1) for transmitting signals are connected between the sensor element 4 in the distal part of the sensor guide wire 1 and a male connector 6 in the male connector region in the proximal part of the guide wire 1.

Figures 2, 3, 4:
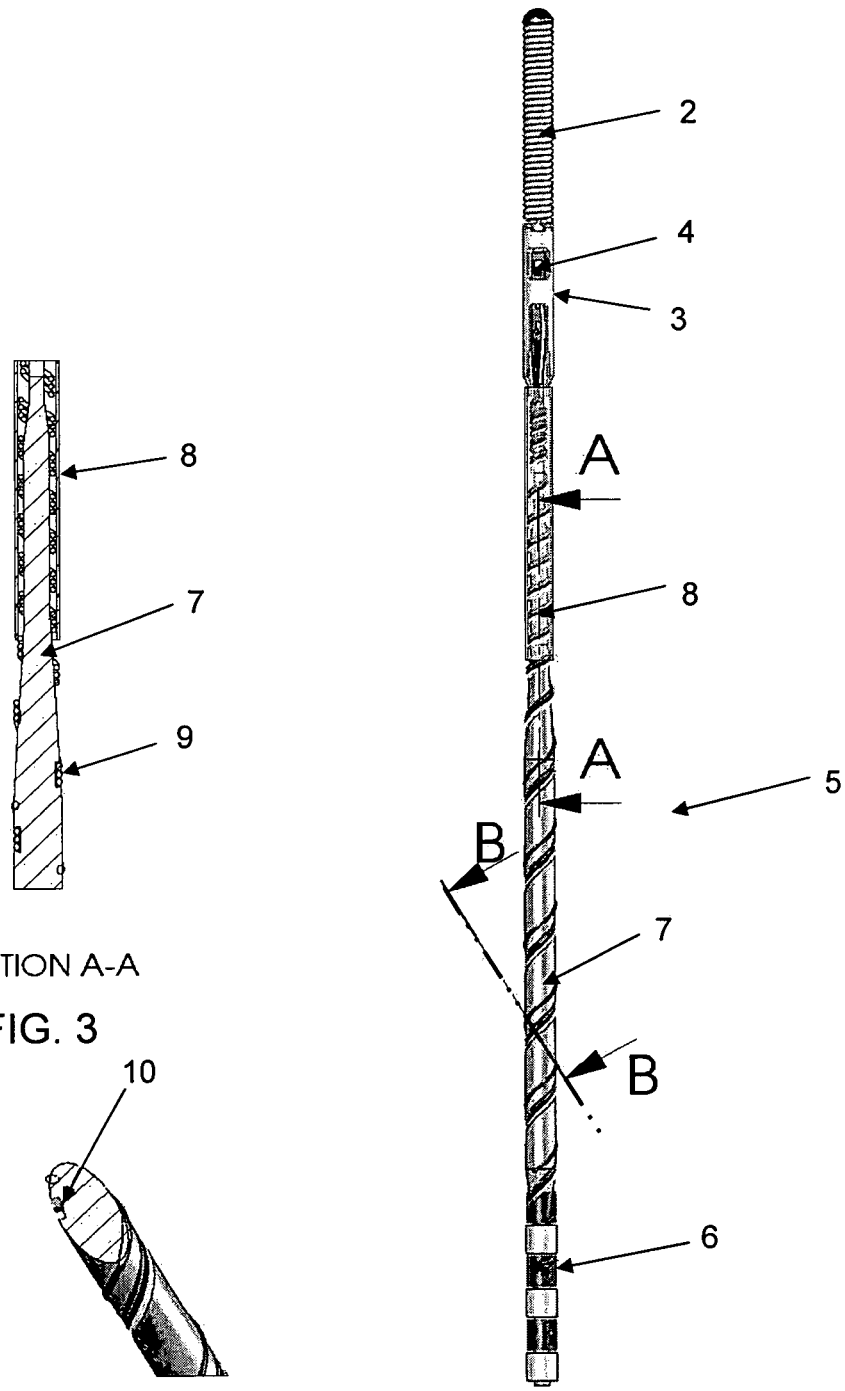
FIG. 2 shows a first embodiment of the present invention.
FIG. 3 is a longitudinal cross-section of a region taken along A-A in FIG. 2.
FIG. 4 shows an oblique transverse cross-section of the sensor guide wire taken along B-B in FIG. 2.

In one embodiment according to the invention as illustrated in FIG. 2, the sensor guide wire comprises an elongated guide wire body 5 arranged between the sensor region and the male connector 6, wherein the at least one electrical micro-cable 9 extends essentially helically around the guide wire body 5 along the length of at least a part of the guide wire 1. By having this arrangement, energy is principally not built up when rotating the sensor guide wire 1 as the sensor guide wire 1 now behaves essentially rotationally symmetrical. A more predictive and reliable behaviour of the sensor guide wire 1 is thus accomplished.

Preferably, the at least one electrical micro-cable 9 extends essentially helically around the guide wire body with a certain pitch, and the pitch of the helical winding may vary along the length of the guide wire 1. The narrower and the more curved vessel into which the sensor guide wire 1 is introduced, the smaller pitch may be required in order to obtain enough flexibility. The pitch variation is thus inter alia based on the vessel geometry. Advantageously, the at least one electrical micro-cable 9 extends essentially helically with 0.5-4 windings per centimetre along the length of the guide wire 1. In a still more preferred embodiment, the at least one electrical micro-cable 9 extends essentially helically with 1-2 windings per centimetre along the length of the guide wire 1. In a further embodiment, the at least on electrical micro-cable 9 extends essentially helically along the length of the guide wire, with a winding per length unit that is a combination of the above described windings.

In one embodiment, the guide wire body 5 is a core wire 7 running along at least a part of the sensor guide wire 1. The core wire is preferably made from a metal, such as stainless steel, or a superelastic metal, e.g. Nitinol®, and may be ground. The mechanical properties (e.g. flexibility and strength) of the sensor guide wire 1 will mainly be determined from the material, design and dimensions of the core wire 7.

In the embodiment illustrated in FIG. 2, the core wire 7 is provided with one or several essentially helical grooves 10 extending along at least a part of the length of the core wire 7, to accommodate the at least one electrical micro-cable 9. The micro-cable(s) 9 are thus disposed in the groove(s). As no proximal tube around the core wire 7 is used, it is possible to increase the diameter of the core wire 7 compared to core wires in prior art sensor guide wires. Increased core diameter is beneficial since a material in wire form in general reaches better mechanical properties than the same material in tube form. This increase of diameter gives further advantages when the ability to withstand stress and pushability are considered. The effect of this embodiment is inter alia that the micro-cables 9 may be fixed to the core wire 7 without any negative impact on the rotational movement (i.e. the sensor guide wire 1 becomes "quasi symmetric" as it behaves as it is rotationally symmetric). The grooves may be made by machining or by forming a metal strip in a helical manner, and may be shaped in different ways to mate with the micro-cable(s) 9, e.g. with rounded or angular edges.

In one embodiment according to the invention the at least one micro-cable 9 extends both accommodated in the above-explained grooves 10 in the core wire 7, and further around the core wire 7 in an essentially helical manner. This embodiment is further illustrated in FIG. 2, where the micro-cables 9 are connected to a proximal male connector 6 and extends helically in grooves 10 along the core wire 7, and changes to extend along the core wire 7 without grooves in a more distal part of the sensor guide wire 1, before the micro-cables 9 connects to the sensor element 4 in the sensor region. FIG. 3 shows a longitudinal cross-section of a region taken along A-A in FIG. 2, where the transition zone is shown in detail. In an advantageous embodiment, as illustrated in FIGS. 2 and 3, part of the extension of the micro-cable(s) 9 along the core wire 7 is encompassed by a coated polymer sleeve, a coating or tubing 8. The sleeve, coating or tubing may also cover the jacket 3 and part of the tip 2, and may, in some cases, also encompass the at least one micro-cable 9 extending in the grooves 10 of the core wire 7, and also the core wire 7 itself.

According to a further embodiment, a proximal tube 13 is arranged around the core wire 7. The core wire 7 and the wound accommodated micro-cables 9 are then protected under the proximal tube 13.

Figures 5, 6:
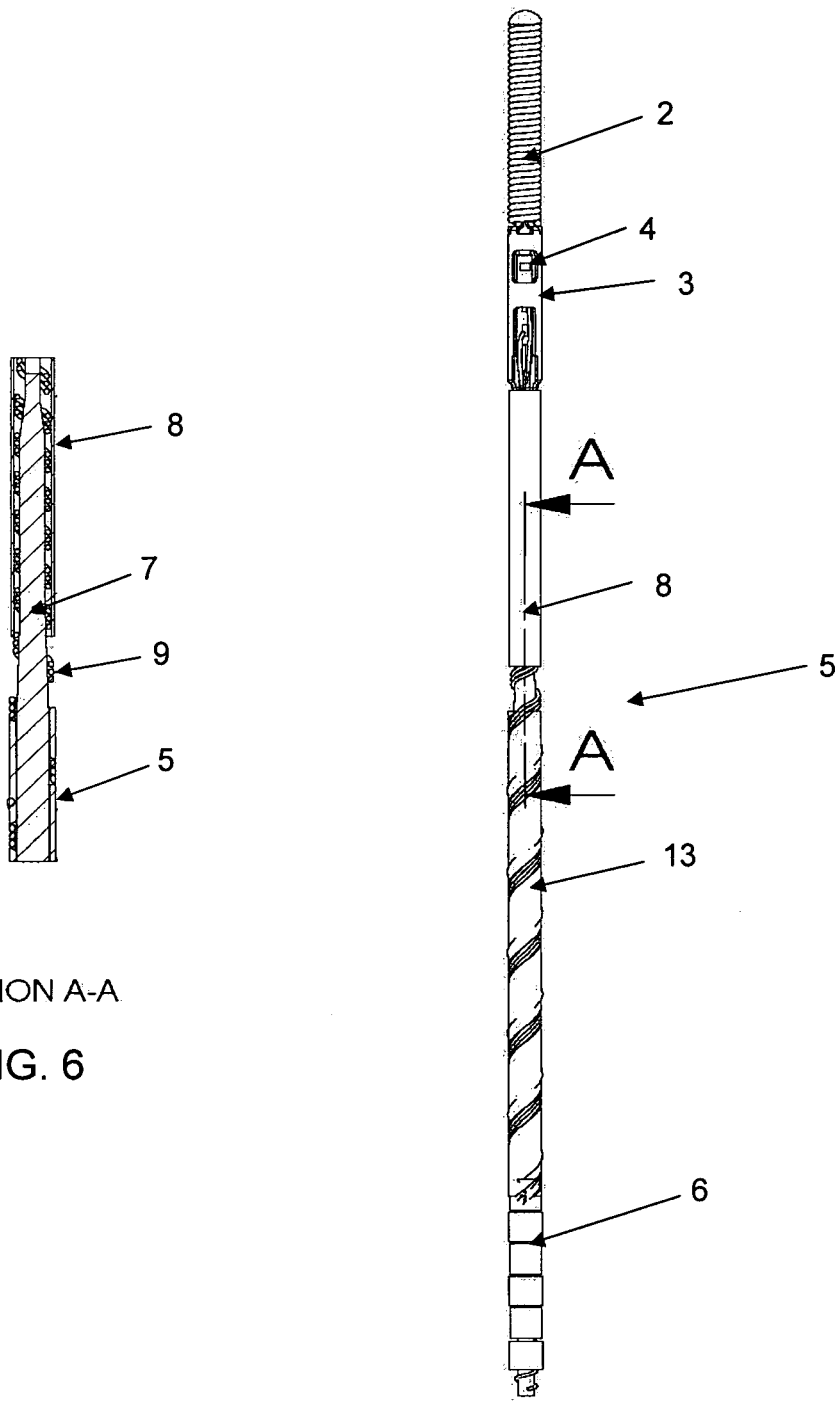
FIG. 5 shows a second embodiment of the present invention.
FIG. 6 is a longitudinal cross-section of a region taken along A-A in FIG. 5.

According to one embodiment illustrated in FIG. 5, the guide wire body 5 is a proximal tube 13 running along at least a part of the sensor guide wire 1. Preferably, the proximal tube 13 is provided with one or several essentially helical grooves along at least a part of the length of the proximal tube 13, to accommodate the at least one electrical micro-cable 9. In one embodiment, the grooves extend along the whole length of the proximal tube 13. The micro-cable(s) 9 are thus disposed in the groove(s). Thus, the micro-cables 9 can be fixed relative the guide wire body 5 without negative impact on the rotational movement, i.e. the sensor guide wire 1 is now essentially quasi-symmetric. The grooves may be made by machining or by forming a metal strip in a helical manner, and may be shaped in different way to mate with the micro-cable(s) 9, e.g. with rounded or angular edges.

In one embodiment, when several micro-cables 9 are used, it is possible to have grooves spaced from each other to e.g. separate power cables and signal transmitting cables. This embodiment can be seen from FIG. 2-6, where three micro-cables 9 are lying next to each other, and one micro-cable 9 is spaced a small distance from the other three. The machining of the grooves 10 in the core wire 7 can be seen in detail from FIG. 4, which shows an oblique transverse cross-section of the sensor guide wire 1 taken along B-B in FIG. 2.

In one embodiment, a core wire 7 is arranged within the proximal tube 13. As the micro-cables 9 are accommodated in grooves in the proximal tube 13, it is possible to increase the diameter of the core wire 7. The outer diameter of the sensor guide wire 1 is generally limited by the vessel geometry and the use of other intravascular catheters, i.e at most 0.35 mm. This possible increase in diameter gives rise to an improved adaptability to different requirements of withstanding stress and possessing a certain pushability. For example, by having a thicker core wire 7, it is possible to withstand more stress in sharp vessel bends. The tube 13 may be fixed to the core wire 7 by joints, bonding or an adhesive, e.g. glue.

In one embodiment according to the invention, the at least one micro-cable 9 extends both along the proximal tube 13, accommodated in the above-explained grooves, and further around the core wire 7 in an essentially helical manner. This embodiment is further illustrated in FIG. 5, where the micro-cables 9 are attached to a proximal male connector 6 and extends helically in grooves along the tube, and changes to extend along the core wire 7 in a more distal part of the sensor guide wire 1 before the micro-cables 9 connects to the sensor element 4 in the sensor region. FIG. 6 shows a longitudinal cross-section of a region taken along A-A in FIG. 5, where the transition zone is shown in detail. In an advantageous embodiment, as illustrated in FIGS. 5 and 6, part of the extension of the micro-cable(s) 9 along the core wire 7 is encompassed by a coated polymer sleeve, a coating or tubing 8. The sleeve, coating or tubing may also cover the jacket 3 and part of the tip 2.

In the embodiments exemplified in the figures, the at least one micro-cable 9 is wound helically along the sensor guide wire 1. It is however possible to have some part or parts of the at least one micro-cable 9 to extend essentially straight or having another extension that deviates from the exemplified helically, or spirally, extending micro-cable(s) 9. However, the requirement for having this embodiment is that the sensor guide wire 1 maintains its essentially rotational symmetrical shape and reduces the risk of having a flip.

Figures 7, 8, 9:
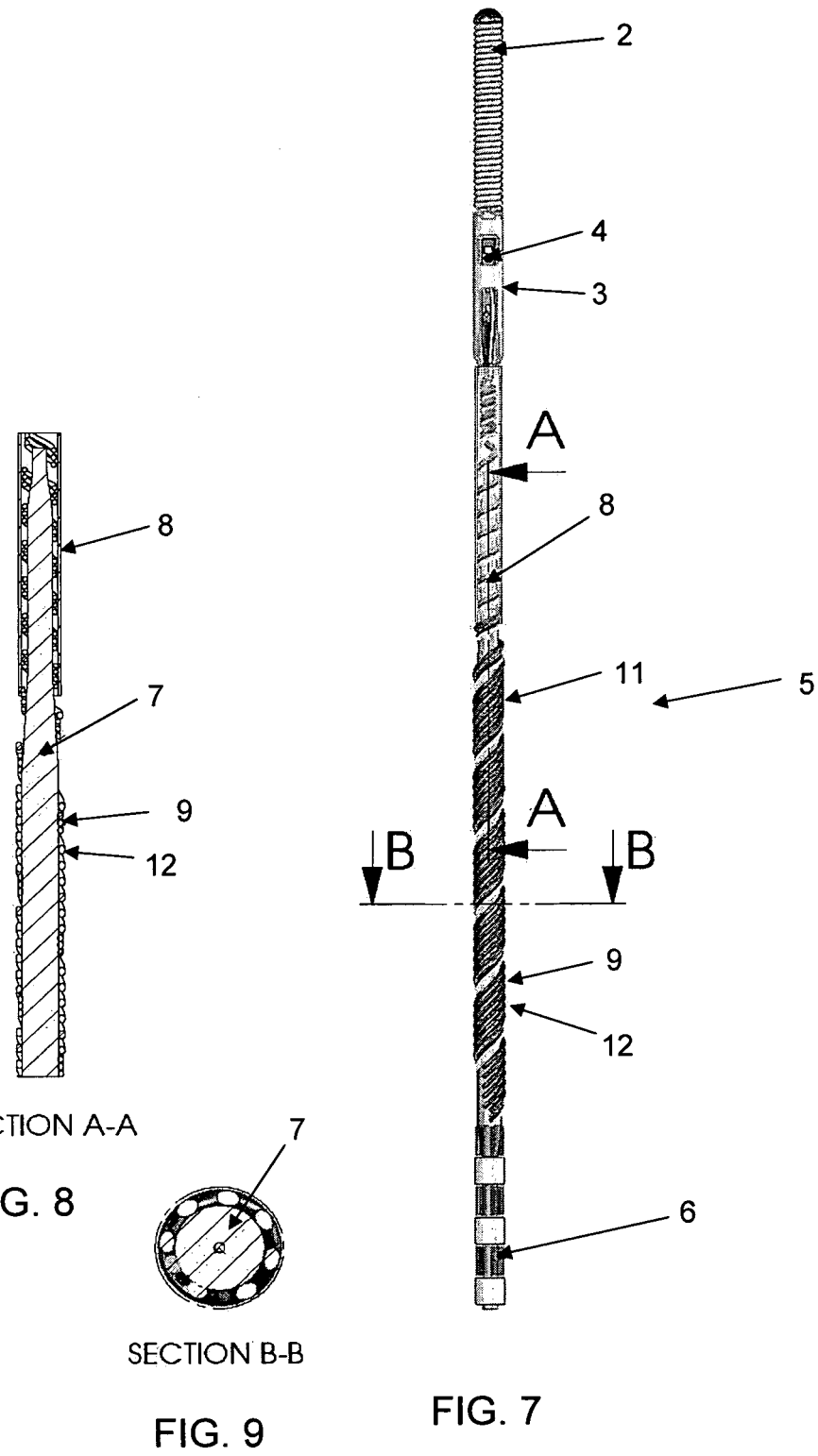
FIG. 7 shows a third embodiment of the present invention.
FIG. 8 is a longitudinal cross-section of a region taken along A-A in FIG. 7.
FIG. 9 shows a transverse cross-section of the sensor guide wire taken along B-B in FIG. 7.

The electrical micro-cables 9, which are essentially helically wound around the guide wire body 5, may in one embodiment illustrated in FIG. 7 be provided with support fibres 12, in order to hold the electrical micro-cables 9 in place in spaced relationship. Preferably the support fibres 12 are provided at each consecutive wound of the electrical micro-cables 9. Consequently, in this embodiment it is possible to have a larger diameter of the core wire 7 than in conventional design. A quasi-rotational symmetry is obtained, which renders an increased controllability of the sensor guide wire 1 possible. In one embodiment according to the invention as illustrated in FIG. 7, the micro-cables 9 extends helically wound both with support fibres 12 along the guide wire body 5 and without support fibres 12 further along a more distal part of the guide wire body 5. In a further embodiment, the support fibres 12 are made from a high strength high elastic modulus material, e.g. aramid or carbon fiber.

FIG. 8 shows a longitudinal cross-section of a region taken along A-A in FIG. 7, where the transition zone between the windings is shown. In an advantageous embodiment, as illustrated in FIGS. 7 and 8, part of the micro-cable(s) 9 wound along the guide wire body 7 is encompassed by a coated polymer sleeve, a coating or tubing 8. Preferably, the guide wire body 5 is a core wire 7. FIG. 9 shows a transverse cross-section of the sensor guide wire taken along B-B in FIG. 7, where the core wire 7, the wounded micro-cables and the support fibres 12 can be seen in cross-section.

The micro-cables 9 as well as the support fibres 12 may in one embodiment be provided with a shrink tubing 11 enclosing at least part of the micro-cables 9 and the support fibres 12, and/or may be (thermally) bonded or glued to the guide wire body 5.

As has been explained above in some embodiments, the at least one electrical micro-cable 9 may be provided with a shrink tubing enclosing at least part of the electrical micro-cable(s) 9 and the guide wire body 5. An example of this embodiment is illustrated in FIG. 10. This shrink tubing protects the micro-cables 9 and the guide wire body 5 from blood etc. in the vessels and holds the micro-cables 9 in place. A transverse cross-section of the sensor and guide wire assembly taken along A-A in FIG. 10 can be seen from FIG. 11.

According to one embodiment, a coated polymer sleeve, coating or tubing 8 covers at least part of a distal part of the sensor guide wire 1.

In appropriate cases, the electrical micro-cable(s) 9 may be fastened to the core wire 7 by bonding or gluing. The micro-cable(s) 9 may also be bonded or glued to the essentially helical grooves in the core wire 7 or proximal tube 13.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A sensor guide wire for an intravascular measurement of a physiological variable in a living body, comprising:
   a sensor region in a distal part of the sensor guide wire,
   a sensor element arranged in said sensor region,
   a male connector at a proximal part of said sensor guide wire,
   at least one electrical micro-cable electrically connecting said male connector to said sensor element, and
   an elongated core wire or tube arranged between said sensor region and said male connector, wherein at least one helical groove is formed in an outer surface of the elongated core wire or tube so as to extend helically along at least a part of the elongated core wire or tube,
   wherein said at least one electrical micro-cable extends helically around said elongated core wire or tube along a length of at least part of the sensor guide wire, and
   wherein at least a part of said at least one electrical micro-cable is disposed in the helical groove of the elongated core wire or tube.

2. The sensor guide wire according to claim 1, wherein said at least one electrical micro-cable extends helically around said elongated core wire or tube with a certain pitch, and wherein said pitch of the helical extending micro-cable varies along the length of the at least part of the sensor guide wire.

3. The sensor guide wire according to claim 2, wherein said at least one electrical micro-cable extends helically with 0.5-4 windings per centimeter along the length of the at least part of the sensor guide wire.

4. The sensor guide wire according to claim 3, wherein said at least one electrical micro-cable extends helically with 1-2 windings per centimeter along the length of the at least part of the sensor guide wire.

5. The sensor guide wire according to claim 1,
   wherein the sensor guide wire comprises the elongated core wire,
   wherein the at least one helical groove is formed in the outer circumferential surface of the elongated core wire, and
   wherein said at least one electrical micro-cable extends helically around said elongated core wire, and
   wherein at least a part of said at least one electrical micro-cable is disposed in the helical groove of the elongated core wire.

6. The sensor guide wire according to claim 5,
   wherein said elongated core wire includes a proximal portion and a distal portion, a diameter of the proximal portion being greater than a diameter of the distal portion,
   wherein the at least one helical groove is located in the proximal portion of the elongated core wire, and
   wherein the at least one electrical micro-cable is disposed in the at least one helical groove in the proximal portion of the elongated core wire, and the at least one electrical micro-cable extends without the at least one helical groove in the distal portion of the elongated core wire.

7. The sensor guide wire according to claim 5, wherein a proximal tube is arranged around said elongated core wire.

8. The sensor guide wire according to claim 1,
   wherein the sensor guide wire comprises the elongated tube, wherein the at least one helical groove is formed in the outer circumferential surface of the elongated tube, and
wherein said at least one electrical micro-cable extends helically around said elongated tube, and
wherein at least a part of said at least one electrical micro-cable is disposed in the helical groove of the elongated tube.

9. The sensor guide wire according to claim 8,
wherein a core wire is arranged within said elongated tube,
wherein the at least one electrical micro-cable extends around the core wire in a location distal of the proximal tube.

10. The sensor guide wire according to claim 9, wherein said at least one helical groove extends along a whole length of said elongated tube, to accommodate said at least one electrical micro-cable.

11. The sensor guide wire according to claim 8, wherein a core wire is arranged within said elongated tube.

12. The sensor guide wire according to claim 6, wherein said at least one helical groove is made by machining.

13. The sensor guide wire according to claim 6, wherein said at least one helical groove is made by forming a metal strip in a helical manner.

14. A sensor guide wire for an intravascular measurement of a physiological variable in a living body, comprising:
a sensor region in a distal part of the sensor guide wire,
a sensor element arranged in said sensor region,
a male connector at a proximal part of said sensor guide wire,
a plurality of electrical micro-cables electrically connecting said male connector to said sensor element, and
an elongated guide wire body arranged between said sensor region and said male connector,
wherein said plurality of electrical micro-cables extend helically around the elongated guide wire body along a length of at least part of the guide wire, and
wherein the sensor guide wire further comprises at least one support fiber that is helically wound around at least a part of the elongated guide wire body along with the plurality of electrical micro-cables, the at least one support fiber holding the electrical micro-cables in place in a spaced relationship over at least a part of the elongated guide wire body.

15. The sensor guide wire according to claim 14, wherein the sensor guide wire comprises a plurality of the support fibers, and the support fibers are provided at each consecutive winding of said electrical micro-cables.

16. The sensor guide wire according to claim 14, wherein the at least one support fiber is made from aramid or carbon fiber.

17. The sensor guide wire according to claim 1, wherein a shrink tubing encloses at least part of said at least one electrical micro-cable and said elongated core wire or tube.

18. The sensor guide wire according to claim 1, wherein the at least one electrical micro-cable is fastened to the elongated core wire or tube by bonding or gluing.

19. The sensor guide wire according to claim 1, wherein a coated polymer sleeve, a coating or a tubing covers at least part of the distal part of said sensor guide wire.

20. The sensor guide wire according to claim 1, wherein the at least one electrical micro-cable has a circular cross-section.

21. The sensor guide wire according to claim 1, wherein the at least one electrical micro-cable is directly connected to the sensor element.

22. The sensor guide wire according to claim 1, wherein the at least one electrical micro-cable has a constant cross-section extending from the male connector to the sensor element.

23. The sensor guide wire according to claim 1, wherein, in at least a portion of the sensor guide wire, the at least one electrical micro-cable is a radially outermost element of the sensor guide wire.

24. The sensor guide wire according to claim 1, wherein the sensor element comprises a blood pressure sensor configured to sense a magnitude of a patient's blood pressure.

25. An intravascular medical assembly, comprising:
a sensor guide wire according to claim 1; and
an intravascular catheter.

26. A sensor guide wire for an intravascular measurement of a physiological variable in a living body, comprising:
a sensor region in a distal part of the sensor guide wire,
a sensor element arranged in said sensor region,
a male connector at a proximal part of said sensor guide wire,
at least one electrical micro-cable electrically connected to said male connector and electrically connected to said sensor element, and
an elongated guide wire body arranged between said sensor region and said male connector,
wherein said at least one electrical micro-cable extends helically around said guide wire body along a length of at least part of the sensor guide wire, and
wherein, in at least a portion of the sensor guide wire, the at least one electrical micro-cable is a radially outermost element of the sensor guide wire.

27. The sensor guide wire according to claim 26, wherein the at least one electrical micro-cable has a constant cross-section extending from the male connector to the sensor element.

28. The sensor guide wire according to claim 26, wherein said guide wire body is a core wire running along the at least part of the sensor guide wire, and wherein said core wire is provided with one or more helical grooves extending along at least part of a length of the core wire, to accommodate said at least one electrical micro-cable.

29. The sensor guide wire according to claim 1, wherein an overall length of the guide wire is between 1171 mm and 2555 mm.

30. The sensor guide wire according to claim 1, wherein the external-most diameter of the sensor guide wire is between 0.25 mm and 0.35 mm.

31. The sensor guide wire according to claim 14, wherein each micro-cable has a constant cross-sectional area for the entire distance that the respective micro-cable extends between the sensor element and the male connector.

32. The sensor guide wire according to claim 14,
wherein said guide wire body includes a proximal portion and a distal portion, a diameter of the proximal portion being greater than a diameter of the distal portion,
wherein, the plurality of electrical micro-cables are helically wound along with the at least one support fiber in the proximal portion of the guide wire body, and the electrical micro-cables are helically wound without the at least one support fiber in the distal portion of the guide wire body.

33. A sensor guide wire for an intravascular measurement of a physiological variable in a living body, comprising:
a sensor region in a distal part of the sensor guide wire,
a sensor element arranged in said sensor region,
a connector at a proximal part of said sensor guide wire, at least one signal transmitting line connecting said connector to said sensor element, and an elongated core wire or tube arranged between said sensor region and said connector, wherein at least one helical groove is formed in an outer surface of the elongated core wire or tube so as to extend helically along at least a part of the elongated core wire or tube, wherein said at least one signal transmitting line extends helically around said elongated core wire or tube along a length of at least part of the sensor guide wire, and wherein at least a part of said at least one signal transmitting line is disposed in the helical groove of the elongated core wire or tube.

34. A sensor guide wire for an intravascular measurement of a physiological variable in a living body, comprising:

a sensor region in a distal part of the sensor guide wire,
a sensor element arranged in said sensor region,
a connector at a proximal part of said sensor guide wire,
at least one signal transmitting line connecting said connector to said sensor element, and
an elongated guide wire body arranged between said sensor region and said connector,
wherein said at least one signal transmitting line extends helically around said guide wire body along a length of at least part of the sensor guide wire, and
wherein, in at least a portion of the sensor guide wire, the at least one signal transmitting line is a radially outermost element of the sensor guide wire.

* * * * *